(12) United States Patent
Kurosaki et al.

(10) Patent No.: US 11,103,215 B2
(45) Date of Patent: Aug. 31, 2021

(54) ULTRASOUND IMAGE DIAGNOSIS APPARATUS, MEDICAL IMAGE DIAGNOSIS APPARATUS, AND COMPUTER PROGRAM PRODUCT

(71) Applicant: Canon Medical Systems Corporation, Otawara (JP)

(72) Inventors: Tatsuru Kurosaki, Nasushiobara (JP); Minori Izumi, Shioya-gun (JP); Takashi Koyakumaru, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 268 days.

(21) Appl. No.: 16/047,700

(22) Filed: Jul. 27, 2018

(65) Prior Publication Data
US 2019/0029648 A1    Jan. 31, 2019

(30) Foreign Application Priority Data
Jul. 28, 2017   (JP) .............................. JP2017-146133

(51) Int. Cl.
*A61B 8/00*    (2006.01)
*G06K 9/32*    (2006.01)
(Continued)

(52) U.S. Cl.
CPC ............ *A61B 8/469* (2013.01); *A61B 8/5223* (2013.01); *G06K 9/3233* (2013.01); *A61B 8/14* (2013.01); *A61B 8/463* (2013.01); *A61B 8/483* (2013.01); *A61B 8/488* (2013.01); *A61B 8/5207* (2013.01); *G06K 2009/366* (2013.01); *G06K 2209/05* (2013.01)

(58) Field of Classification Search
None
See application file for complete search history.

(56) References Cited

U.S. PATENT DOCUMENTS

2007/0293755 A1* 12/2007 Shirahata ............... A61B 6/466
                                                                   600/425
2008/0267499 A1  10/2008 Deischinger et al.
(Continued)

FOREIGN PATENT DOCUMENTS

JP          2002-224116 A       8/2002

OTHER PUBLICATIONS

Japanese Office Action dated Jun. 15, 2021, issued in Japanese Patent Application No. 2017-146133.

*Primary Examiner* — Joel F Brutus
(74) *Attorney, Agent, or Firm* — Oblon, McClelland, Maier & Neustadt, L.L.P.

(57) ABSTRACT

According to one embodiment, an ultrasound image diagnosis apparatus includes a boundary detection unit, a measurement unit, and a display control unit. The boundary detection unit detects the boundary of a structure in a subject based on volume data generated from a reflected signal of ultrasound waves transmitted toward inside of the subject. The measurement unit measures the size of the structure based on the boundary detected by the boundary detection unit. The display control unit displays the cross section of the structure according to a definition that is set in the advance and related to the size of the structure measured by the measurement unit.

16 Claims, 11 Drawing Sheets

(51) Int. Cl.
  *A61B 8/08* (2006.01)
  *G06K 9/36* (2006.01)
  *A61B 8/14* (2006.01)

(56) References Cited

U.S. PATENT DOCUMENTS

| | | | | |
|---|---|---|---|---|
| 2014/0171800 | A1* | 6/2014 | Kondou | A61B 8/14 |
| | | | | 600/440 |
| 2016/0063695 | A1* | 3/2016 | Lee | A61B 8/463 |
| | | | | 382/131 |
| 2017/0061607 | A1* | 3/2017 | Eskandari | G06T 5/30 |

* cited by examiner

ULTRASOUND IMAGE DIAGNOSIS APPARATUS, MEDICAL IMAGE DIAGNOSIS APPARATUS, AND COMPUTER PROGRAM PRODUCT

CROSS-REFERENCE TO RELATED APPLICATION

This application is based upon and claims the benefit of priority from Japanese Patent Application No. 2017-146133, filed on Jul. 28, 2017; the entire contents of which are incorporated herein by reference.

FIELD

Embodiments described herein relate generally to an ultrasound image diagnosis apparatus, a medical image diagnosis apparatus, and a computer program product.

BACKGROUND

In recent years, a medical image diagnosis apparatus has been used to collect information on the inside of a subject and image the inside of the subject based on the information to generate a medical image. Examples of the medical image diagnosis apparatus include an X-ray computed tomography (CT) system, magnetic resonance imaging (MRI) equipment, an ultrasound diagnosis apparatus, and the like. Among them, the ultrasound image diagnosis apparatus is configured to receive reflected signals of ultrasound waves transmitted toward a structure inside the subject, and generate an ultrasound image relating to the structure.

Examples of the ultrasound image generated include a three-dimensional image that illustrates the structure three-dimensionally and also a two-dimensional ultrasound image (MPR image) obtained by multi-planar reconstruction (MPR). In addition, the size of the structure inside the subject depicted on the MPR image, such as a follicle or a heart chamber, may be measured by using the MPR image.

The measurement is automatically performed by the ultrasound image diagnosis apparatus. However, in the case of measuring the axial length of the structure in particular, the operator has to check whether it has been accurately measured as he/she intended.

This is because, a structure that is actually large may sometimes appear small on the MPR image depending on the position of a cross section. Besides, when the contour of the structure is automatically detected, the automatic detection function may not correctly detect it depending on artifacts at the time of imaging and the state of luminance of the structure. In addition, in the case of the follicle mentioned above, there are a plurality of structures. Therefore, the operator's check work is more troublesome as compared to the case where there is only one structure. As a result, the time taken for diagnosis may be prolonged.

DETAILED DESCRIPTION

In general, according to one embodiment, an ultrasound image diagnosis apparatus includes a boundary detection unit, a measurement unit, and a display control unit. The boundary detection unit detects the boundary of a structure in a subject based on volume data generated from a reflected signal of ultrasound waves transmitted toward inside of the subject. The measurement unit measures the size of the structure based on the boundary detected by the boundary detection unit. The display control unit displays the cross section of the structure according to a definition that is set in the advance and related to the size of the structure measured by the measurement unit.

In the following, exemplary embodiments are described in detail with reference to the drawings.

Incidentally, any of the X-ray CT system, the MRI equipment, and the ultrasound image diagnosis apparatus can be used to acquire volume data by photographing a structure inside a subject and measure the size of the structure base on the volume data. Accordingly, what is described in the following embodiments can be applied to all of them. For example, the following embodiments can be applied to the examination of the four chambers of the heart (left ventricle, left atrium, right ventricle, right atrium) using the X-ray CT system. In the following, the ultrasound image diagnosis apparatus is described as an example from among these apparatuses.

[Configuration of Ultrasound Image Diagnosis Apparatus]

Figure 1:
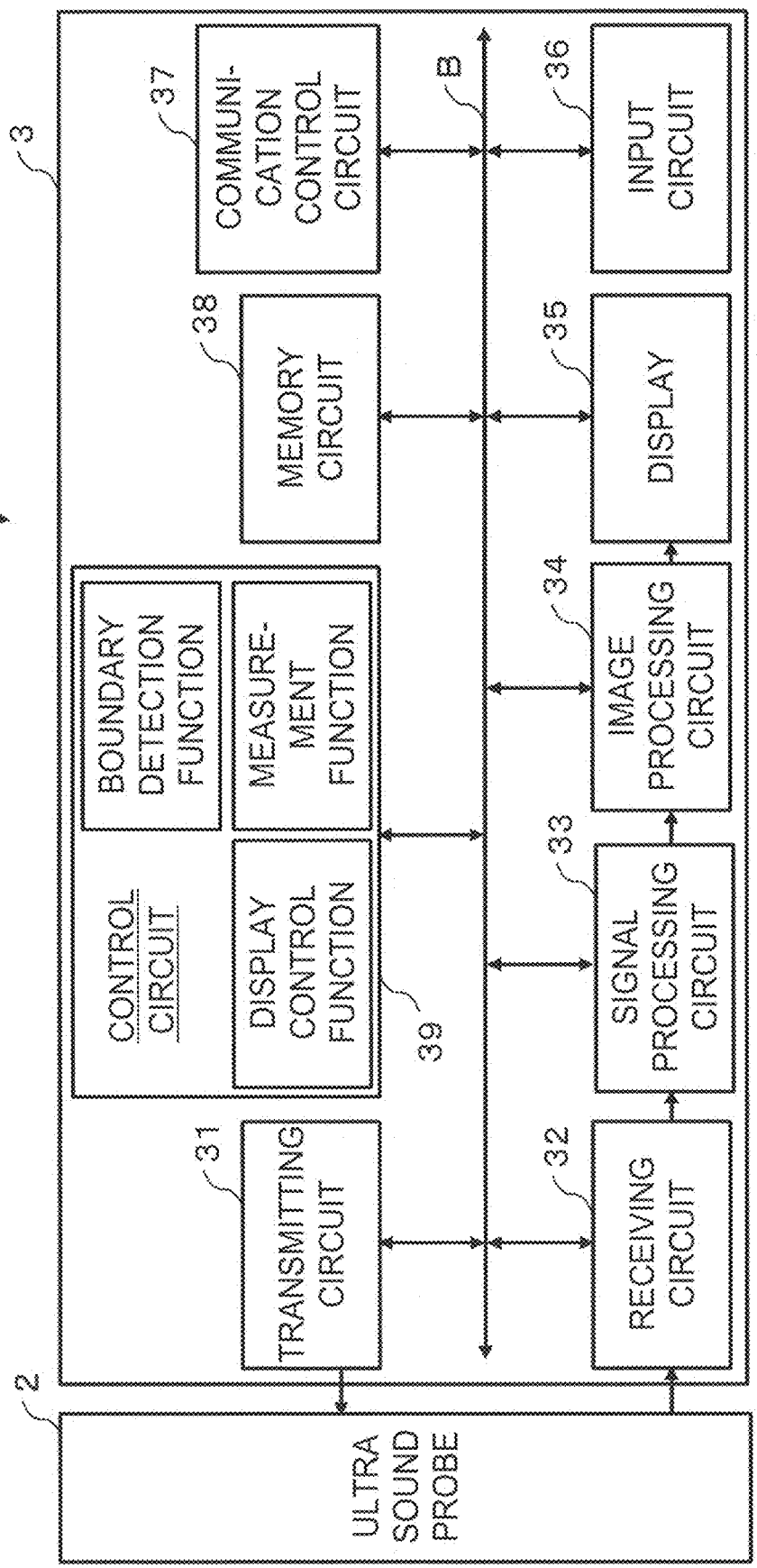
FIG. 1 is a functional block diagram illustrating the overall configuration of an ultrasound image diagnosis apparatus according to an embodiment.

FIG. 1 is a functional block diagram illustrating the overall configuration of an ultrasound image diagnosis apparatus 1 according to an embodiment. As illustrated in FIG. 1, the ultrasound image diagnosis apparatus 1 includes an ultrasound probe 2 configured to transmit and receive ultrasound waves to and from a subject, and a main body 3. The ultrasound probe 2 is detachably connected to the main body 3.

The ultrasound image diagnosis apparatus 1 is an example of a medical image diagnosis apparatus that is capable of noninvasively examining a structure inside the subject, the blood flow state, and the like. The ultrasound image diagnosis apparatus 1 is configured to transmit ultrasound waves toward the inside of a subject from the ultrasound probe 2 having transducers (piezoelectric transducers) at the tip, and receive reflected waves caused by acoustic impedance mismatch inside the subject through the transducers of the ultrasound probe 2. The ultrasound image diagnosis apparatus 1 generates an ultrasound image based on the received signal.

The ultrasound probe 2 is configured to transmit ultrasound waves into the subject through each of the ultrasound transducers to scan a scan area, and receive reflected waves from the subject as echo signals. Examples of the scan include various types of scans such as B mode scan and Doppler mode scan. Besides, examples of the ultrasound probe 2 include a sector scan probe, a linear scan probe, a convex scan probe, and the like, and one of them is arbitrarily selected according to the site to be diagnosed.

The main body 3 includes a transmitting circuit 31, a receiving circuit 32, a signal processing circuit 33, an image processing circuit 34, a display 35, and an input circuit 36. The transmitting circuit 31 is configured to transmit a drive signal to the ultrasound probe 2. The receiving circuit 32 is configured to receive echo signals from the ultrasound probe 2. The signal processing circuit 33 is configured to process the echo signals. The image processing circuit 34 is configured to generate an ultrasound image. The display 35 is configured to display the two-dimensional or three-dimensional ultrasound image generated. The display 35 also displays the result of the measurement of a structure and the like. The input circuit 36 is configured to receive an input signal as being operated by the operator such as an examiner.

The main body 3 further includes a communication control circuit 37 configured to control the exchange of signals with other devices (not illustrated), a memory circuit 38, and a control circuit 39 configured to control each part. These circuits are connected to a bus B and can exchange various signals. The functions of each circuit are described below in further detail.

Under the control of the control circuit 39, the transmitting circuit 31 generates a drive signal for causing the ultrasound probe 2 to generate ultrasound waves, i.e., an electric pulse signal (hereinafter referred to as "drive pulse") to be applied to each of the piezoelectric transducers. The transmitting circuit 31 transmits the drive pulse to the ultrasound probe 2. The transmitting circuit 31 includes circuits such as, for example, a reference pulse generating circuit, a delay control circuit, a drive pulse generating circuit, and the like (not illustrated), and those circuits perform the functions mentioned above.

The receiving circuit 32 receives an echo signal, i.e., received signal from the ultrasound probe 2. The receiving circuit 32 performs phasing addition on the received signal, and outputs the resultant signal to the signal processing circuit 33.

The signal processing circuit 33 generates various types of data using the received signal from the ultrasound probe 2 fed by the receiving circuit 32, and outputs the data to the image processing circuit 34 and the control circuit 39. The signal processing circuit 33 includes, for example, a B mode processing circuit (or Bc mode processing circuit), a Doppler mode processing circuit, a color Doppler mode processing circuit, and the like (not illustrated). The B mode processing circuit visualizes amplitude information of the received signal, and generates data based on a B mode signal. The Doppler mode processing circuit extracts Doppler shift frequency component from the received signal, and applies fast Fourier transform (FFT) or the like thereto, thereby generating Doppler signal data of blood flow information. The color Doppler mode processing circuit visualizes the blood flow information based on the received signal, and generates data based on a color Doppler mode signal.

The image processing circuit 34 generates two-dimensional or three-dimensional ultrasound images related to the scan area based on the data supplied from the signal processing circuit 33. For example, the image processing circuit 34 generates volume data related to the scan area from the supplied data. Then, from the volume data generated, the image processing circuit 34 generates data of a two-dimensional ultrasound image by multi-planar reconstruction (MPR) and data of a three-dimensional ultrasound image by volume rendering. The image processing circuit 34 outputs the two-dimensional or three-dimensional ultrasound image to the display 35. Examples of the ultrasound image include a B mode image, a Doppler mode image, a color Doppler mode image, an M mode image, and the like.

The display 35 displays various images such as an ultrasound image generated by the image processing circuit 34 and an operation screen (e.g., graphical user interface (GUI) configured to receive various instructions from the operator) under the control of the control circuit 39. The display 35 is also capable of displaying the result of the automatic measurement of the size of a structure in such a way that is easy to understand. As the display 35, for example, a liquid crystal display (LCD), an organic electroluminescence (EL) display, or the like can be used.

The input circuit 36 receives various input operations made by the operator to provide, for example, an instruction to display an image or switch images, designation of the mode, various settings, and the like. For example, GUI, input devices such as buttons, a keyboard, a trackball, a touch panel displayed on the display 35, or the like can be used as the input circuit 36.

Incidentally, in the embodiment, the display 35 and the input circuit 36 are each described as one constituent element of the ultrasound image diagnosis apparatus 1 as illustrated in FIG. 1; however, it is not so limited. The display 35 need not necessarily be a constituent element of the ultrasound image diagnosis apparatus 1, but may be separated from the ultrasound image diagnosis apparatus 1. The input circuit 36 may be a touch panel displayed on the separate display.

The communication control circuit 37 enables the ultrasound image diagnosis apparatus 1 to communicate with, for example, medical image diagnosis apparatuses (modalities), servers, medical image processing apparatuses, and the like (not illustrated) each connected to a communication network (not illustrated). Information and medical images exchanged between the communication control circuit 37 and other devices via the communication network may be in conformity with any standard such as digital imaging and communication in medicine (DICOM) and the like.

The memory circuit 38 is formed of, for example, a semiconductor or a magnetic disk. The memory circuit 38 stores programs to be executed by the control circuit 39 and data. The memory circuit 38 also stores information on the positions of three intersecting cross sections that are displayed on the display 35 as two-dimensional ultrasound images, and the like. Further, the memory circuit 38 stores the result of measurement indicating the size of a structure measured by the measurement function of the control circuit 39 (described later).

The control circuit 39 comprehensively controls each part of the ultrasound image diagnosis apparatus 1. The control circuit 39 causes the display 35 to display the ultrasound image generated by the image processing circuit 34. Besides, the control circuit 39 receives an instruction from the operator through the input circuit 36 as an input signal, and controls each circuit to perform desired operation.

The control circuit 39 performs a boundary detection function, a measurement function, and a display control function. The control circuit 39 uses the boundary detection function before performing the automatic measurement of a structure described next. Specifically, after the operator photographs structures of the subject, the control circuit 39 automatically detects the boundary between the hypoechoic area and the hyperechoic area of volume data acquired to detect the boundary between adjacent structures.

The control circuit 39 measures the size of each structure using the measurement function based on the boundary detected by the boundary detection function. The "size" of the structure measured herein refers to the result obtained by measuring the volume, length (axial length), and the like of the structure. As to the content of the measurement such as whether to measure the volume or to measure the axial length, it can be arbitrarily set in advance. Besides, calculation may be performed based on the content of the measurement to obtain a calculation result. The content of the measurement and the calculation result are stored in the memory circuit 38.

With the measurement function, for example, the control circuit 39 measures the volume of the structure by calculating the contour of the structure and then filling the inside thereof with polyhedrons. For another example, the control circuit 39 performs principal component analysis on the apex of the structure to obtain the first, second, and third principal components, and measures the length thereof as the axial length of the structure. Note that the measurement function is implemented by known technology, and the size of each structure may be measured using any other methods.

Then, in order to distinguish the measured structures from one another, the control circuit 39 changes the display by, for example, applying a color or a pattern to each of the structures, giving a serial number, or the like using the measurement function so that the operator can easily recognize them. Thus, the control circuit 39 displays three intersecting cross sections, which are displayed as two-dimensional images, on the display 35 in such a manner that the operator can distinguish the structures from one another.

After measuring the size of each structure by the measurement function and displaying the result on the display 35, the control circuit 39 specifies a cross section indicating a value that meets the definition set in advance with respect to a structure designated in a specific cross section and displays it using the display control function according to an instruction from the operator.

The "definition" set in advance refers to a parameter for displaying the measured structure in an appropriate size in relation to other structures. In the case where the size of the structure is represented by the axial length, for example, "maximum axial length", "minimum axial length", "average axial length" and the like may be cited as the definition.

Figure 2:
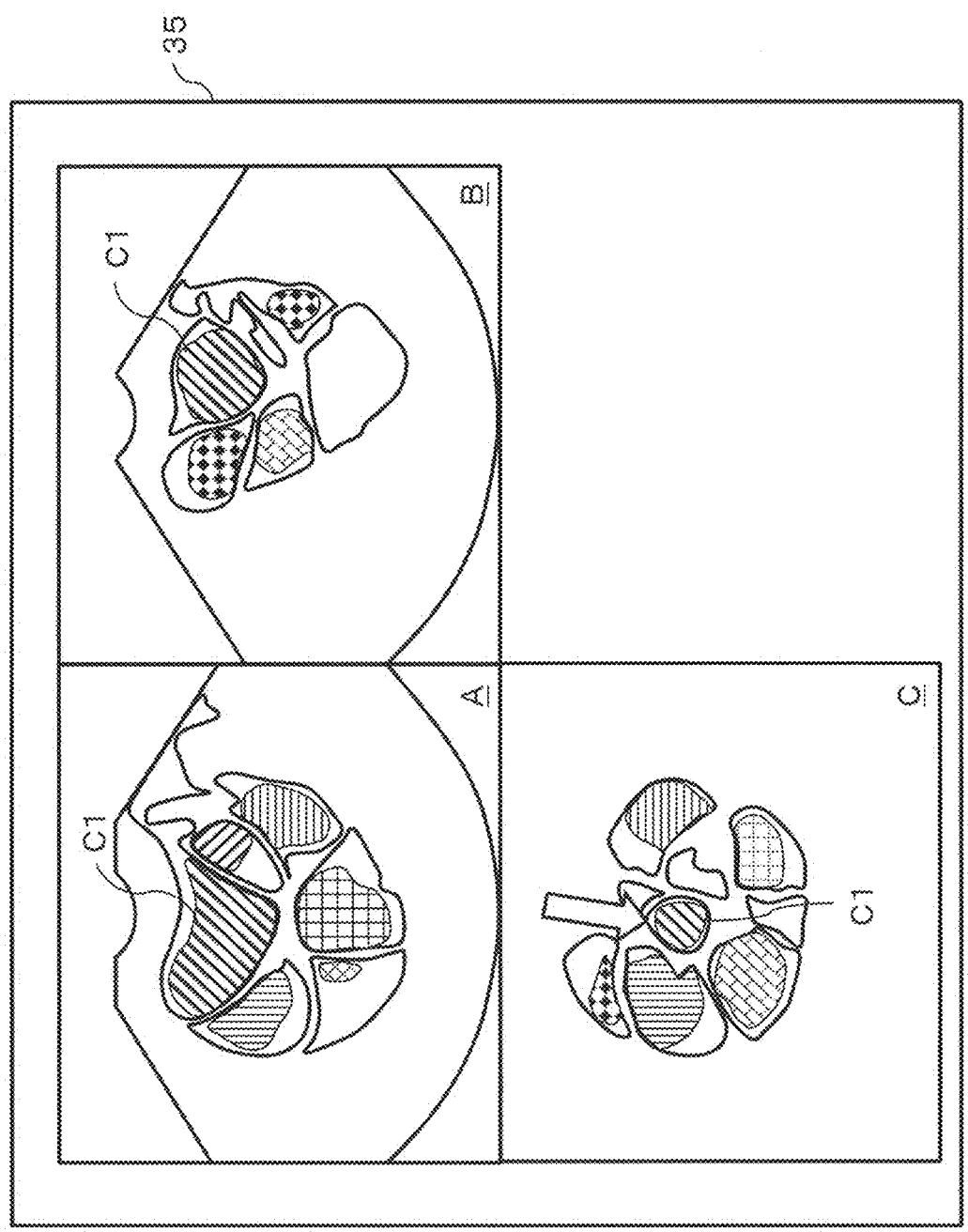
FIG. 2 is a diagram illustrating an example of images displayed when structures are measured, and the operator designates a structure to display an appropriate image on the display according to the definition, in the embodiment.

When two-dimensional images are displayed as three intersecting cross sections on the display 35, the size of the structure may not be displayed properly depending on the positions of the cross sections. This is described below with reference to FIGS. 2 to 4 as an example. FIG. 2 is a diagram illustrating an example of images displayed when structures are measured, and the operator designates a structure to display an appropriate image on the display 35 according to the definition, in the embodiment.

In the example of FIG. 2, the display 35 displays three two-dimensional images. These are ultrasound images each illustrating a cross section obtained by cutting volume data that represents the inside of the subject acquired by imaging with the use of the three intersecting cross sections.

Figure 3:
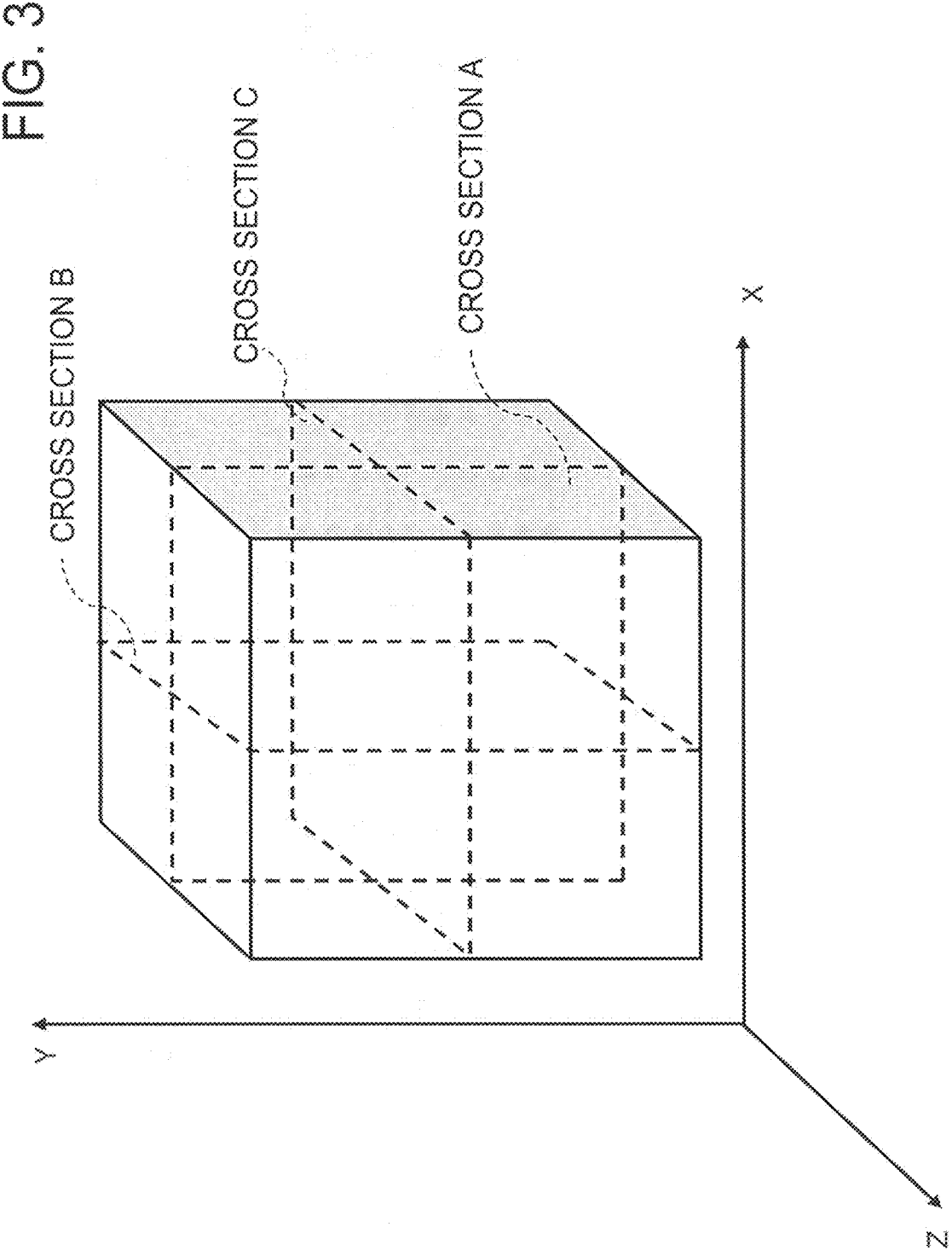
FIG. 3 is an explanatory diagram illustrating the relationship between a three-dimensional image and the three intersecting cross sections, in the embodiment.

FIG. 3 is an explanatory diagram illustrating the relationship between a three-dimensional image and the three intersecting cross sections, in the embodiment. In FIG. 3, the three-dimensional image is indicated by a solid cube. The cube corresponds to a structure C generated by the image processing circuit 34 from volume data acquired by imaging. FIG. 3 also illustrates three directions of X axis, Y axis, and Z axis.

In the structure C, cross section A is represented by the X-Y plane, cross section B is represented by the Y-Z plane, and cross section C is represented by the Z-X plane. The three intersecting cross sections are illustrated as orthogonal three cross sections in FIG. 3. However, the three intersecting cross sections need not necessarily be orthogonal to one another, and any of the planes may be at an angle.

In FIG. 2, among the three intersecting cross sections displayed on the display 35, the one on the upper left is the cross section A, the one on the right side of the cross section A is the cross section B, and the one below the cross section A is the cross section C. That is, for example, the cross section A is a cross section obtained by cutting a structure along the X-Y plane and displayed as a two-dimensional image.

The structures C illustrated in FIG. 2 and other figures are, for example, follicles. All the figures illustrate a plurality of structures C, and each of the structures C is provided with a pattern. In the three intersecting cross sections, those having the same pattern indicate the same structure C. For example, the cross section A contains six structures C, the cross section B contains four structures C, and the cross section C contains five structures C.

In FIG. 2 and other figures, the structures are distinguished by different patterns for convenience of illustration. However, upon displaying the structures on the display 35, they need not necessarily be distinguished by patterns as illustrated in FIG. 2 and other figures. The structures can be displayed to be distinguishable by any other methods such as, for example, color-coding or numbering as described above.

In the cross section A in FIG. 2, the structure having the largest area at the upper center has a pattern of diagonal lines from the lower left to the upper right. This structure is, for example, a structure C1. There are five structures around the structure C1. As they are different structures, they are provided with different patterns. The display control function of the control circuit 39 is described below taking the structure C1 as an example.

When three intersecting cross sections are displayed on the display 35, a position in the structure where the cross sections are located is set in advance. Therefore, upon displaying three two-dimensional images as a three-dimensional image, the control circuit 39 cuts the three-dimensional image at the set position and displays the three intersecting cross sections.

As described above, since the position where the three-dimensional image is to be cut is determined in advance, a large structure is not always displayed large in any of the intersecting cross sections. For example, the structure C1 is illustrated in all the cross sections A, B, and C. However, the structure C1 in the cross section C appears smaller than in the cross sections A and B.

Although the position to be cut is determined in advance, for example, when three intersecting cross sections are displayed on the display 35 before the control circuit 39 performs the automatic measurement of the structure using the measurement function, the operator can move the position as appropriate. However, even if the operator can adjust the position when the cross sections are displayed before the automatic measurement, still there is a possibility that the size of the structure cannot be appropriately illustrated in any of the cross sections.

Consequently, when the operator sees the structure C1 in the cross section C after the automatic measurement, he/she may determine that the size of the structure C1 is not appropriately illustrated. Therefore, in this embodiment, the control circuit 39 performs a process so that the size of the structure is appropriately illustrated in the cross sections by using the display control function.

The structure C1 which is illustrated to be large in the cross sections A and B appears small in the cross section C as indicated by the arrow in the cross section C, and the size is probably not appropriately illustrated in the cross section C. In this case, the operator designates the structure C1 in the cross section C through the input circuit 36.

When the operator has designated the structure C1, an input signal indicating that the structure C1 is designated is sent from the input circuit 36 to the control circuit 39. Having received the input signal, the control circuit 39 starts the process such that the size of the structure C1 is appropriately illustrated in the cross section C by using the display control function.

Specifically, for example, the Z-X plane that represents the cross section C is moved in the Y direction to a position indicating a value conforming to the definition. For example, when it is defined that the structure C1 is to be represented with the maximum axial length, the Z-X plane is moved in the Y direction to a position indicating the maximum axial length of the structure C1 in the Z-X plane. Alternatively, the Z-X plane may be rotated so that the maximum axial length can be represented.

Figure 4:
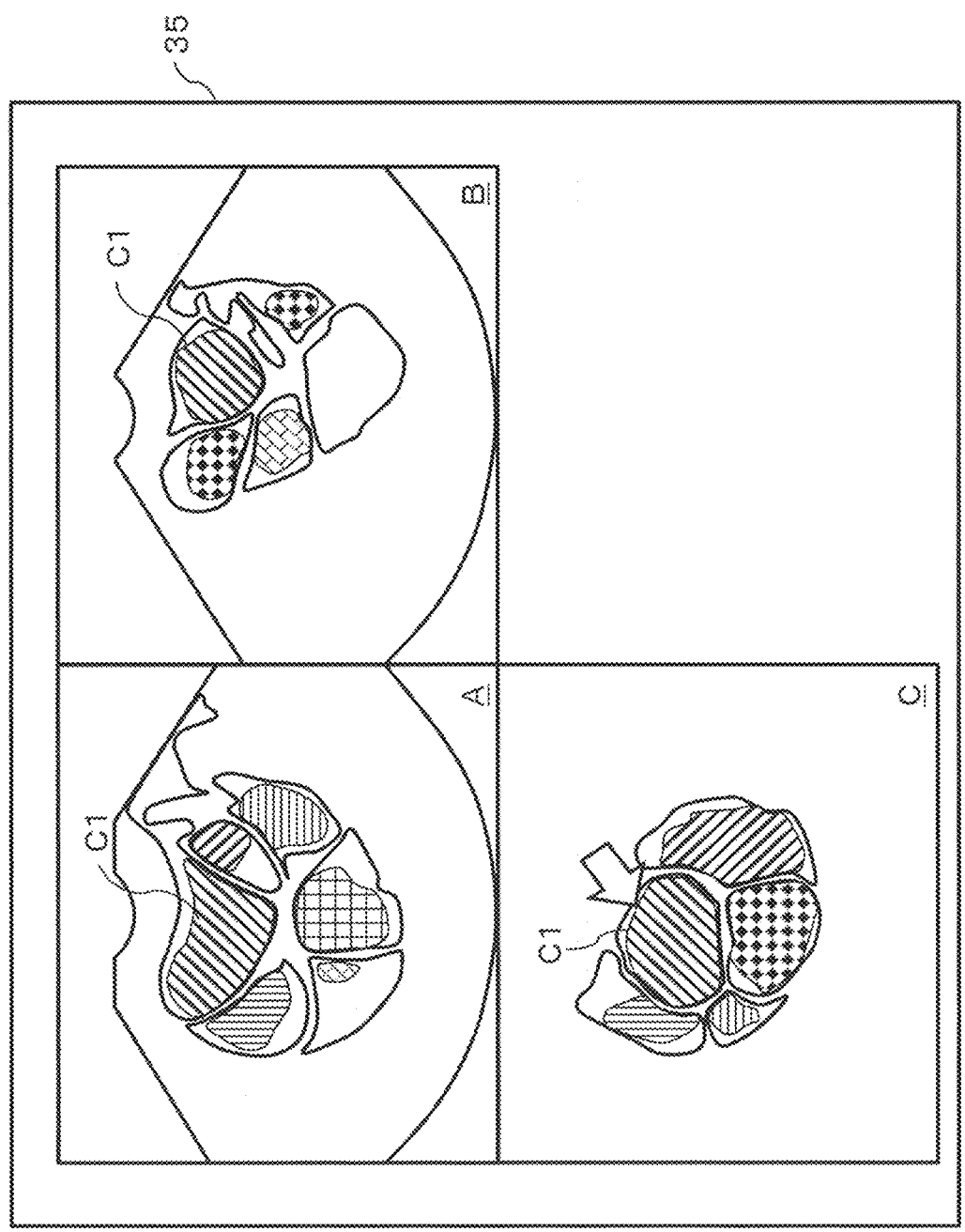
FIG. 4 is a diagram illustrating an example of images displayed when structures are measured, and an appropriate image of a structure designated by the operator is displayed on the display according to the definition, in the embodiment.

FIG. 4 is a diagram illustrating an example of images displayed when structures are measured, and an appropriate image of the structure C1 designated by the operator is displayed on the display 35 according to the definition, in the embodiment. In the cross section C of FIG. 4, the structure C1 is illustrated larger than in the cross section C of FIG. 2. That is, the size indicated in the cross section C of FIG. 4 represents the maximum axial length of the structure C1 in the Z-X plane.

In this manner, the control circuit 39 automatically displays the designated structure in its suitable size on the display 35 using the display control function. Thus, the operator is only required to designate a structure subjected to the processing and does not need to check whether each structure is displayed in an appropriate size on the display 35.

As described above, the operator can directly designate a structure to be subjected to the display optimization of the control circuit 39 for displaying the structure in its suitable size using the display control function. Besides, for example, it is also possible to designate a structure using a list or the like that indicates the size of each structure.

Figure 5:
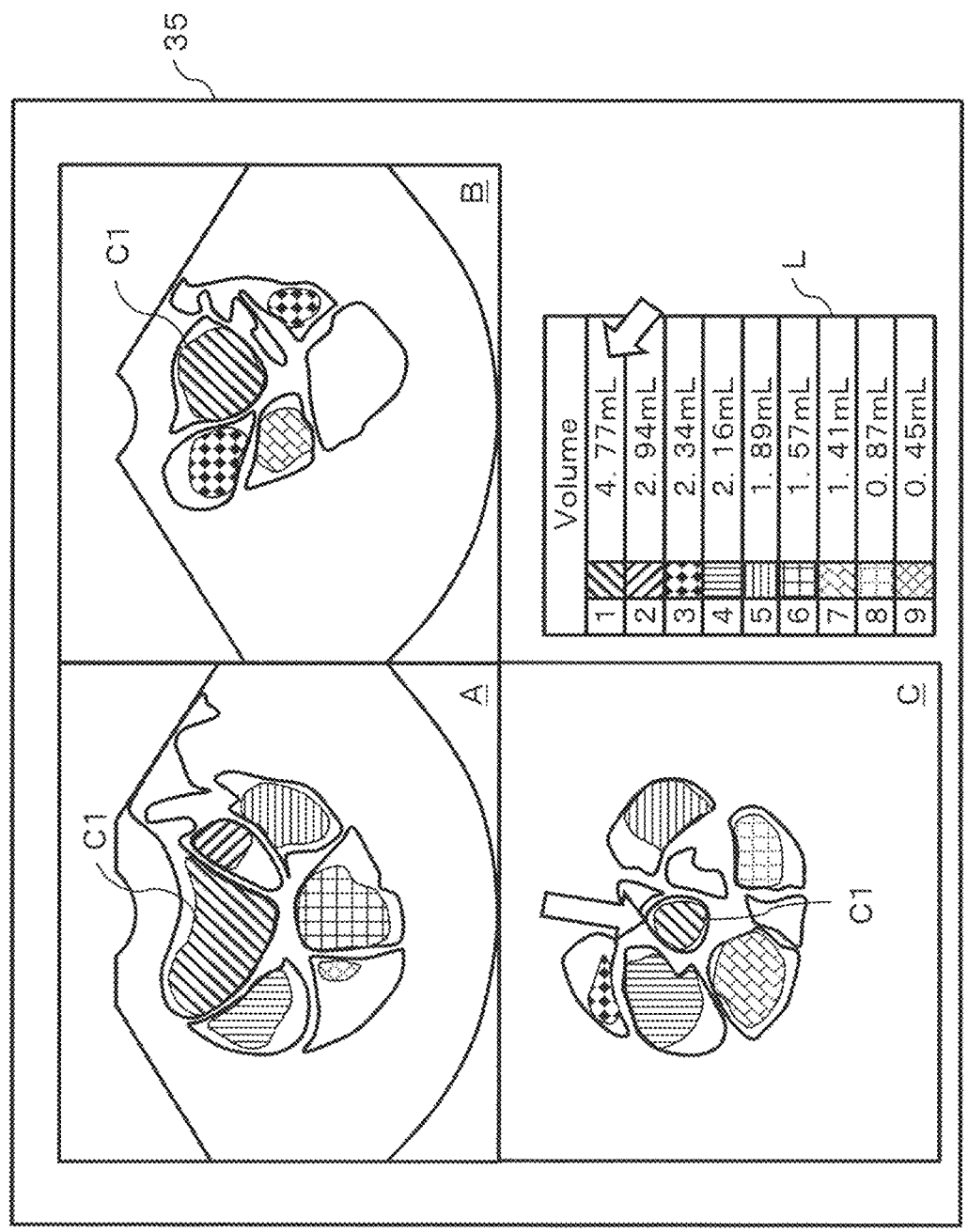
FIG. 5 is a diagram illustrating another example of images displayed when structures are measured, and the operator designates a structure to display an appropriate image on the display according to the definition, in the embodiment.

FIG. 5 is a diagram illustrating another example of images displayed when structures are measured, and the operator designates a structure to display an appropriate image on the display 35 according to the definition, in the embodiment. In FIG. 5, the display 35 displays a list L in addition to the cross sections A, B, and C. The list L illustrates the size (volume) of each structure automatically measured. The size may be the axial length or the surface area as well as the volume.

In FIG. 5, the list L indicates the sizes of nine structures in descending order according to the types of the structures displayed. In addition to the sizes actually measured, the list L also indicates the patterns provided to the structures so that the operator can find the size of each structure at a glance.

Incidentally, the list L displayed on the display 35 need not be as illustrated in FIG. 5. The sizes may be listed in an arbitrary manner, and the display form of the list L on the display 35 can be set arbitrarily.

The operator can select and designate a structure to be displayed on the display 35 in an appropriate size from the list L. In FIG. 5, an arrow is displayed on the list L to indicate that an item corresponding to the structure C1 is designated.

Figure 6:
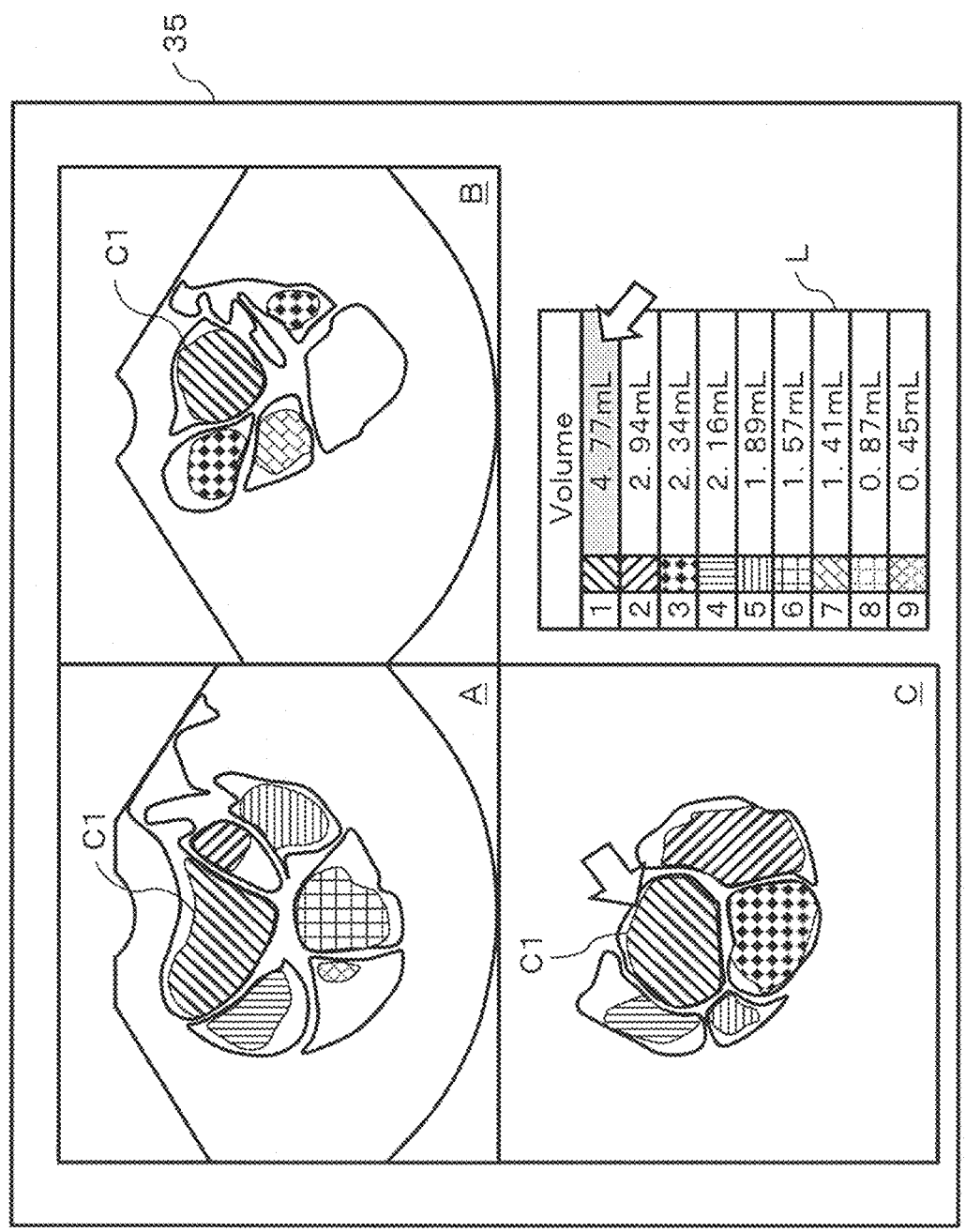
FIG. 6 is a diagram illustrating an example of images displayed when structures are measured, and an appropriate image of a structure designated by the operator is displayed on the display according to the definition, in the embodiment.

FIG. 6 is a diagram illustrating an example of images displayed when structures are measured, and an appropriate image of a structure designated by the operator is displayed on the display 35 according to the definition, in the embodiment. In FIG. 6, the item corresponding to the structure C1 designated by the operator is indicated by a different color to make it clear which item (structure) has been designated.

The control circuit 39 performs the process of displaying the designated structure on the display 35 in its appropriate size by using the display control function. In the cross section C of FIG. 6, it can be seen that the process has been performed for the structure C1.

Figure 7:
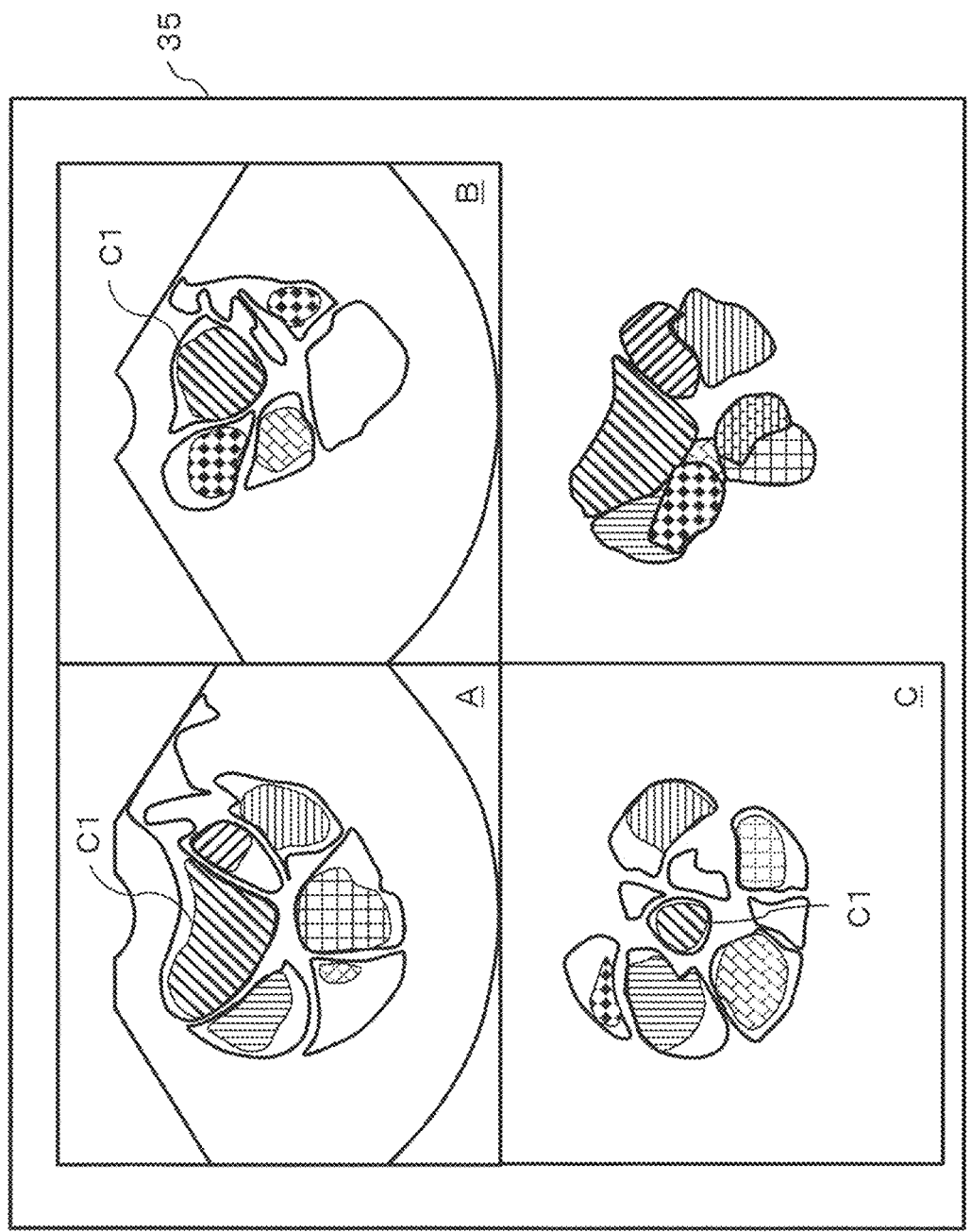
FIG. 7 is a diagram illustrating an example of a three-dimensional image and intersecting cross sections displayed on the display, in the embodiment.

The control circuit 39 can also display a three-dimensional image generated by the image processing circuit 34 on the display 35. FIG. 7 is a diagram illustrating an example of a three-dimensional image and intersecting cross sections displayed on the display 35, in the embodiment. In FIG. 7, the display 35 displays a three-dimensional image in addition to the three intersecting cross sections. Through the display of not only the cross sections but also the three-dimensional image on the display 35, the operator can easily figure out the positional relationship, the relative sizes, and the depth direction of a plurality of structures, which are difficult to know in the two-dimensional images.

Further, the orientation of the three-dimensional image displayed can be changed according to the direction of any of the intersecting cross sections. That is, by using the display control function, the control circuit 39 can display the three-dimensional image as being oriented in the same direction as one of the cross sections selected by the operator. For example, when the operator selects the cross section A, the control circuit 39 changes the orientation of the three-dimensional image so that the cross section A faces the front. Accordingly, when the operator selects a different cross section, the orientation of the three-dimensional image is changed.

The control circuit 39 is also capable of displaying the definition on the structure on the structure designated by the operator and displayed in an appropriate size on the display

Figure 8:
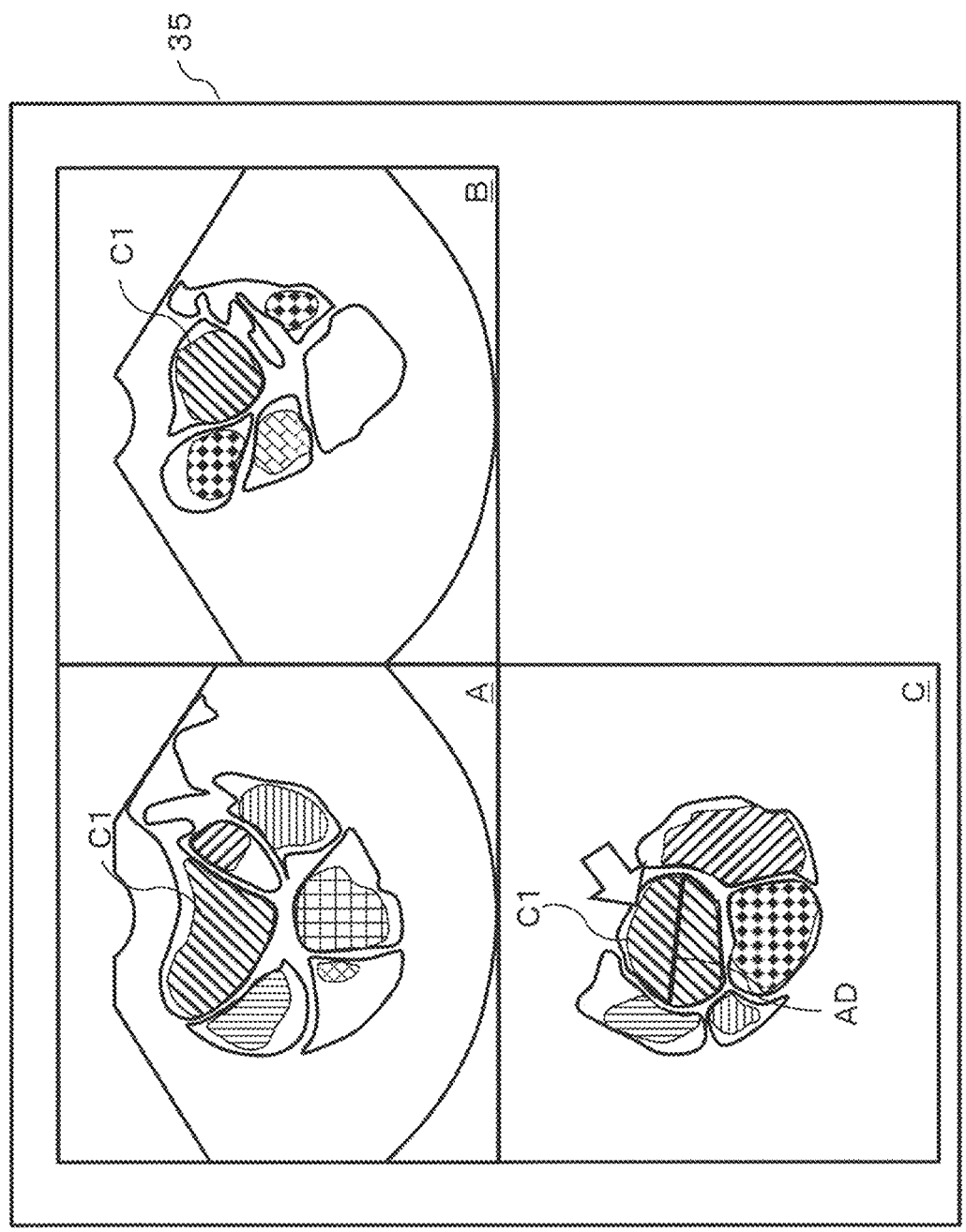
FIG. 8 is a diagram illustrating an example in which the definition content is displayed on a cross section displayed on the display, in the embodiment.

35. FIG. 8 is a diagram illustrating an example in which the definition content is displayed on a cross section displayed on the display 35, in the embodiment.

FIG. 8 illustrates an example in which the structure C1 is displayed in an appropriate size on the cross section C based on the designation by the operator. The definition that is the basis for this display is illustrated on the structure C1. In FIG. 8, a straight line is illustrated on the structure C1 in the cross section C. The straight line is, for example, the maximum axial length AD as the definition. The illustration varies depending on the definition.

In this manner, if the definition is displayed on the display 35 together with the structure that is displayed in an appropriate size according to the designation by the operator, the operator can know the reason why the structure is displayed in this way.

After appropriately displaying the structure designated by the operator, the control circuit 39 can adjust the region of each structure according to adjustment operation by the operator using the display control function.

For example, when the structure is a follicle (egg), the operator has to determine whether the egg is to be collected from its size. Accordingly, the size of the follicle to be collected is set in advance. For example, the lower limit of the size is set as a threshold such that a egg larger than the threshold is to be collected. Then, the control circuit 39 measures the size of a follicle photographed by using the measurement function, and the operator determines whether to collect the egg based on the measurement result. Therefore, each follicle needs to be displayed in an appropriate size on the display 35.

In the case of a egg that is on the borderline as to whether it is to be collected, the egg may be determined to be collected. In this case, in order to clarify that the egg displayed on the display 35 is to be collected, the operator adjusts the display of the measurement result.

Specifically, the operator designates a structure to be adjusted with the input circuit 36. Upon receipt of a signal of designating the structure from the input circuit 36, the control circuit 39 expands a patterned portion by using the display control function to reduce the blank space in the region of the structure. For example, the operator drags the edge of the patterned portion in the region of the structure he/she designated with a mouse or the like to expand it so as to reduce the blank space in the region.

In response to this operation by the operator, the control circuit 39 displays the patterned portion in an enlarged size on the display 35 by using the display control function. Note that the control circuit 39 does not move each of the cross sections A to C in this process, but only expands the patterned portion on the display 35.

In the region of each structure, the patterned portion indicates the size of the structure. Therefore, if the operator excessively expands the patterned portion that is provided with the pattern through the automatic measurement, an error occurs in the measurement result.

Figure 9:
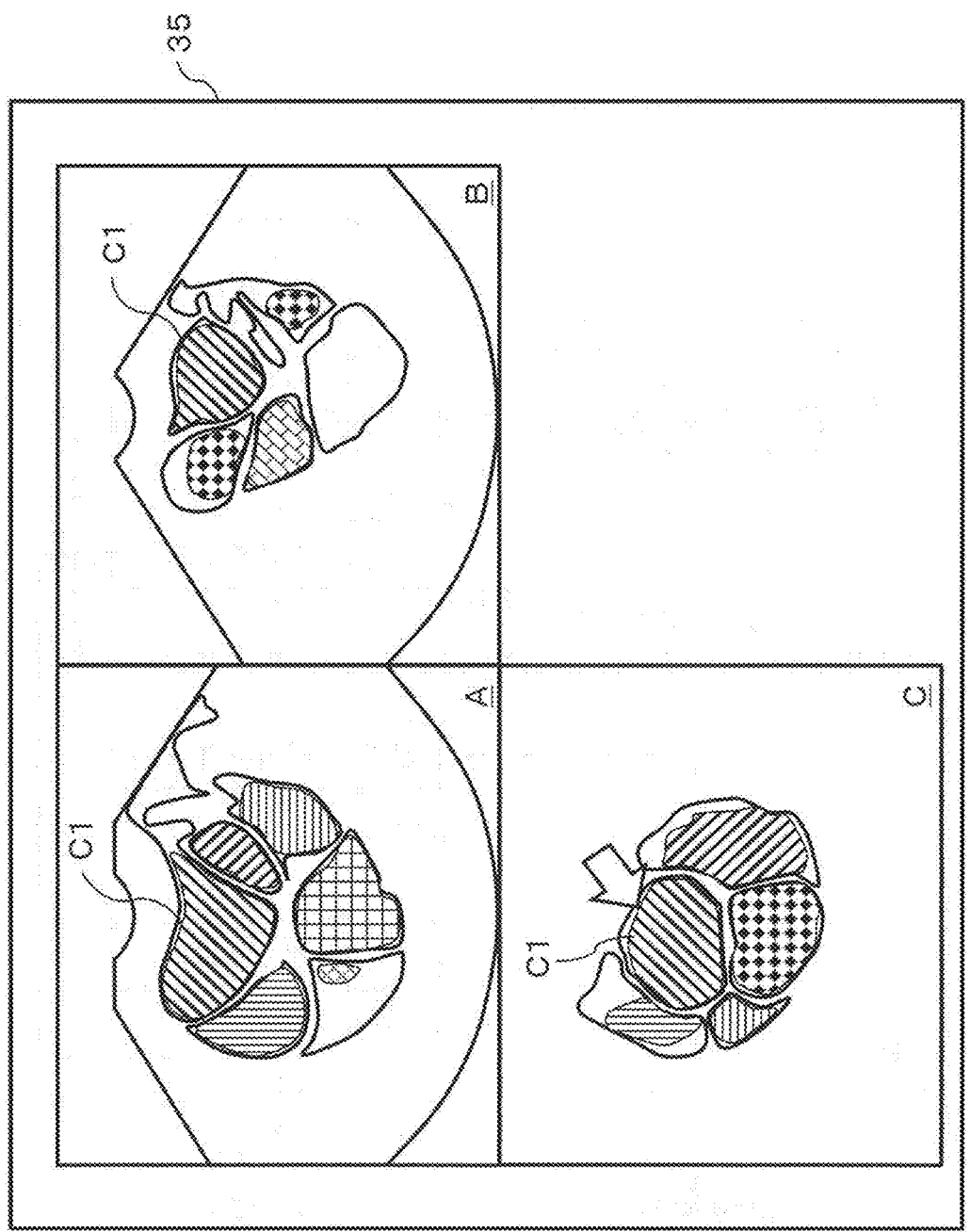
FIG. 9 is a diagram illustrating an example of images displayed when structures are measured, and fine adjustment is performed after an appropriate image of a structure designated by the operator is displayed on the display according to the definition, in the embodiment.

Having determined the extent to which each patterned portion is expanded, the operator expands the patterned portion. For example, it can be seen from the comparison of the A cross section of FIG. 9 with that of FIG. 2 that patterned portions are expanded in many regions of structures.

Meanwhile, in the region of the structure displayed at the lower left in the cross section A, the non-patterned portion is larger than the patterned portion. Therefore, if the patterned portion is expanded to such an extent as to fill the blank space, an ignorable error may be caused in the measurement result. For this reason, the operator has not expanded the patterned portion in the region of the structure.

Note that the patterned portion is expanded within the region of each structure. Even if there is a space around the region of each structure in the display of the display 35, the operator does not expand the patterned portion to outside of the region. In this manner, when the control circuit 39 automatically measures the size of a structure by using the measurement function and the measurement result is not appropriately indicated in the display of the display 35, the operator performs this operation to correct the display.

With the operation as explained so far, a structure designated by the operator is displayed appropriately. However, after having performed the operation, the operator may want to check again as to whether each structure is displayed in an appropriate size. In this case, the control circuit 39 automatically moves the cross section illustrating the structure designated by the operator and displays changes in the size.

Specifically, for example, when the cross section C is moved in the Y direction, the size of the structure C1 in the cross section C varies according to the position of the cross section C unless the structure C1 has the same cross sectional area in the Y direction. That is, as the control circuit 39 moves the cross section C in the Y direction, the size of the structure C1 displayed on the display 35 varies according to the position of the cross section C.

In response to operator's designation of the structure C1, the control circuit 39 automatically moves the cross section in which the structure C1 is designated. Along with the movement of the cross section, the size of the structure C1 changes on the display 35. By viewing changes in the size of the structure C1, the operator can check whether the structure C1 designated is displayed in an appropriate size.

The range in which the control circuit 39 moves the cross section can be set in advance. When the movement range has been set, the cross section that illustrates the structure C1 designated by the operator is moved within the movement range. The operator can stop the movement of the cross section at an arbitrary position.

Incidentally, the boundary detection function, the measurement function, and the display control function of the control circuit 39 can be realized by a computer program that is executed by a processor and stored in a predetermined memory, the memory circuit 38, or the like. The term "processor" as used herein refers to a circuit such as, for example, a dedicated or general central processing unit (CPU) arithmetic circuit (circuitry), an application specific integrated circuit (ASIC), a programmable logic device such as a simple programmable logic device (SPLD) and a complex programmable logic device (CPLD), a field programmable gate array (FPGA), or the like.

The processor reads out, for example, a program stored in the memory circuit 38 or directly incorporated in the circuit of the processor and executes it, thereby realizing the functions. Each processor may be provided with a recording circuit for storing the program. For example, the recording circuit may store a program corresponding to the functions of the signal processing circuit 33 illustrated in FIG. 1. Besides, the configuration of the memory circuit 38 illustrated in FIG. 1 may be employed to store the program. The memory circuit is formed of a storage device, examples of which include a semiconductor memory and a magnetic disk such as a general random access memory (RAM) and a hard disc drive (HDD).

[Operation]

Figure 10:
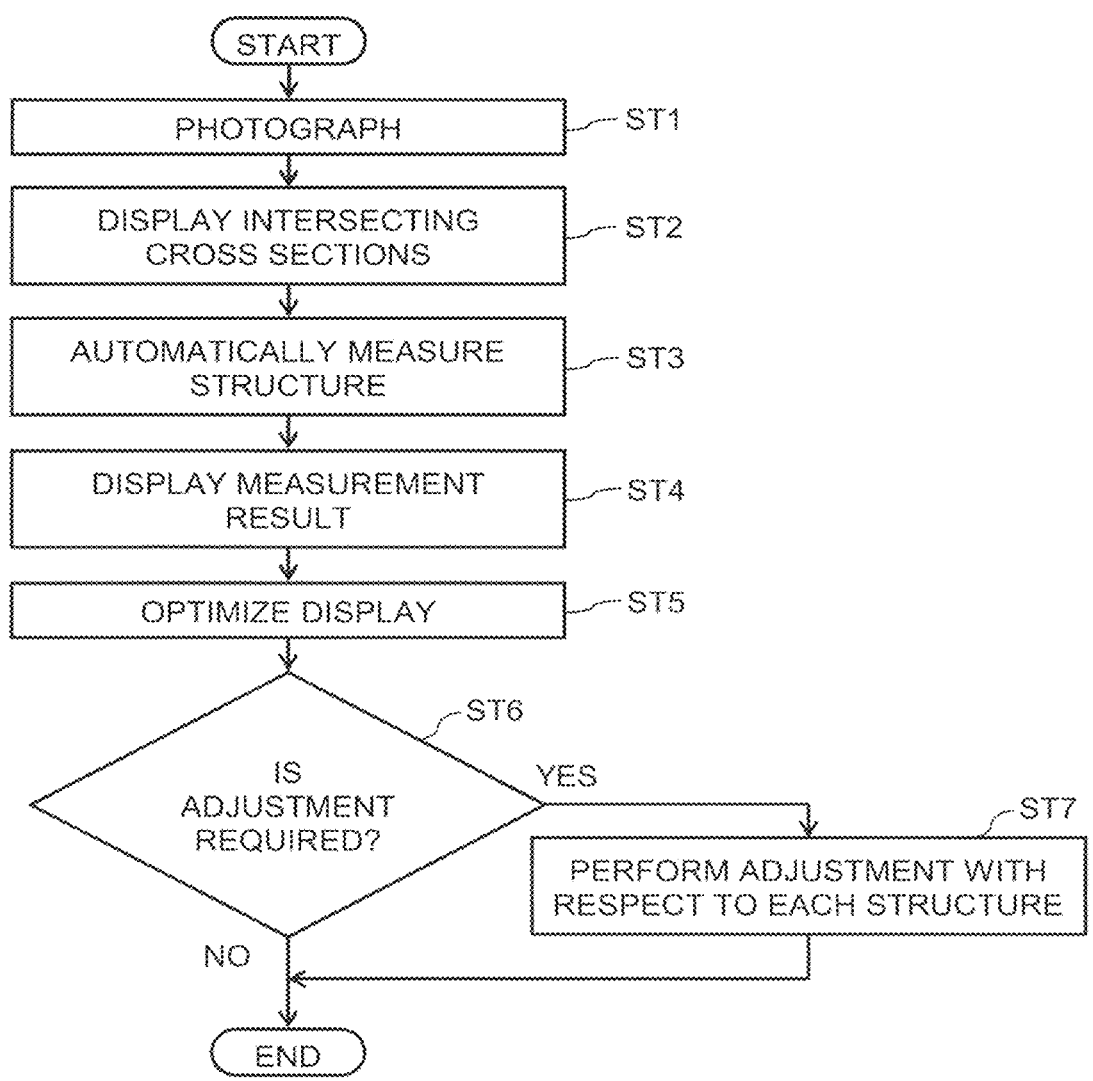
FIG. 10 is a flowchart schematically illustrating the operation of displaying the size of a structure designated in a cross section according to the definition set in advance in the cross section, in the embodiment.
Figure 11:
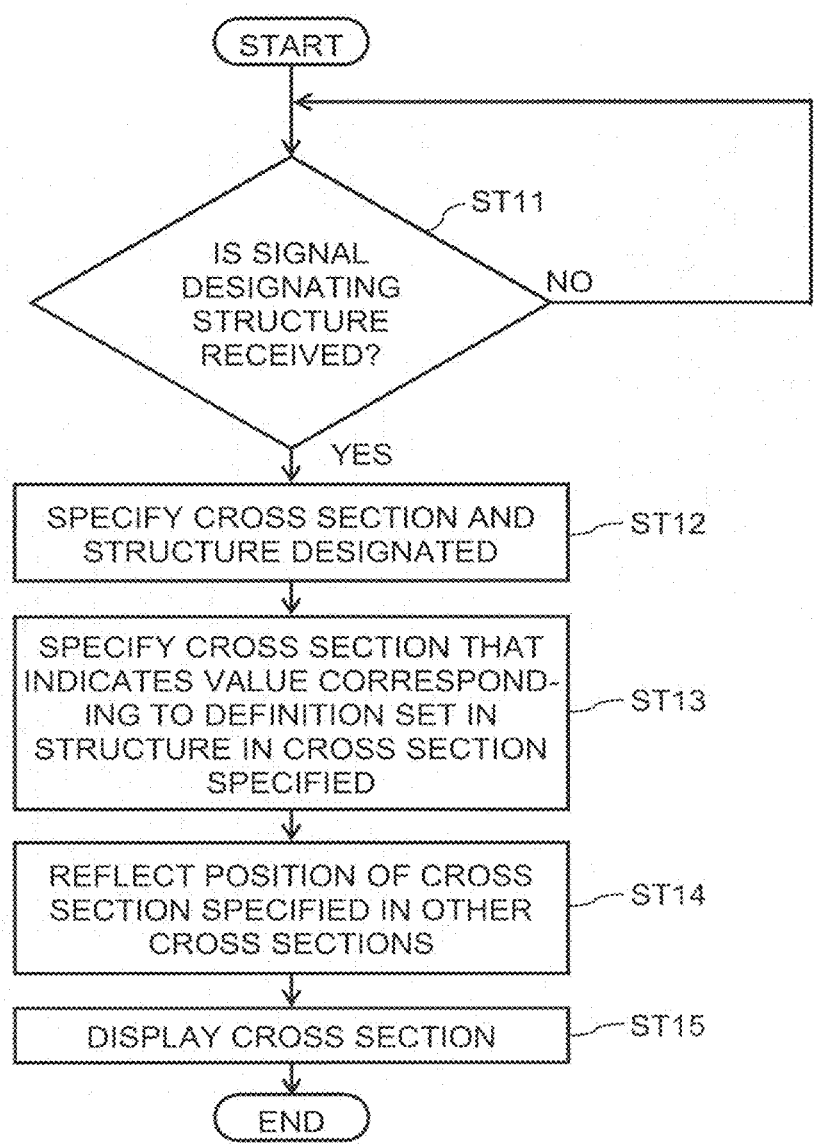
FIG. 11 is a flowchart illustrating the detailed operation of displaying the size of a structure selected in a cross section according to the definition set in advance in the cross section, in the embodiment.

Next, with reference to FIGS. 10 and 11, a description is given of the process of displaying a structure designated by the operator in an appropriate size on the display 35. FIG. 10 is a flowchart schematically illustrating the operation of displaying the size of a structure designated in a cross section according to the definition set in advance in the cross section, in the embodiment. FIG. 11 is a flowchart illustrating the detailed operation of displaying the size of a structure selected in a cross section according to the definition set in advance in the cross section, in the embodiment.

First, with the ultrasound image diagnosis apparatus 1, the operator photographs the inside of the subject by using the ultrasound probe 2 (ST1). Specifically, the transmitting circuit 31 transmits a drive pulse to the ultrasound probe 2. The ultrasound probe 2 receives reflected waves from the subject. The image processing circuit 34 generates an ultrasound image based on the reflected waves, and the image is displayed on the display 35 (ST2). Examples of the ultrasound image displayed include a three-dimensional image and a two-dimensional image illustrating a cross section. It is assumed here, for example, that intersecting cross sections are displayed as illustrated in FIG. 2.

When the ultrasound image is displayed on the display 35, the control circuit 39 detects the boundary of structures displayed using the boundary detection function. Then, the control circuit 39 measures the size of the structures defined by the detection of the boundary (ST3). As described above, the size measured is the volume or the axial length. The control circuit 39 measures the size of the structures by using the measurement function. The operator may set a region of interest (ROI) as to the structures to be automatically measured.

The measurement result is displayed on the display 35 (ST4). For example, the display 35 displays each of the structures with a pattern in three intersecting cross sections as illustrated in FIG. 2. However, the size of the structures (the measurement result) may not be appropriately displayed on the display 35. In this case, the operator designates a target structure to optimize the display (ST5).

When the structures are illustrated in the three intersecting cross sections in such a manner that their sizes can be figured out, some of the structures may not be displayed in an appropriate size. The control circuit 39 determines whether a signal that designates a structure is received from the input circuit 36 operated by the operator (ST11 in FIG. 11). The control circuit 39 specifies a cross section and the structure designated by the operator by using the display control function (ST12).

After that, the control circuit 39 specifies a cross section that indicates a value corresponding to the definition set in the structure in the cross section specified (ST13). Specifically, the control circuit 39 moves or rotates the cross section specified to find a cross section indicating a value that meets a predetermined definition such as the maximum volume or the maximum axial length and specifies it.

When a cross section that properly indicates the size of the structure designed in the cross section is specified, the positions of the other two cross sections are determined at the position thereof. That is, the position of the cross section specified is reflected in the other cross sections (ST14). Then, the display 35 displays the structure in its corresponding size in the cross section specified at the position. In addition, since the position is reflected in the positions of the other two cross sections as described above, the display 35 also displays the structure in its corresponding sizes in the two cross sections (ST15).

When the structure designated by the operator is displayed in an appropriate size in the cross section specified on the display 35, the size of the structure in the other cross sections is also adjusted (ST6 in FIG. 10). This adjustment refers to the above-described expansion of patterned portions, i.e., structures whose size has been measured, performed by the operator.

When the expansion is required (YES in ST6), the operator performs the adjustment with respect to each structure (ST7). On the other hand, when all structures are displayed in their appropriate sizes on the display 35, and no adjustment is required (NO in ST6), the optimization of the structure size is completed.

By the process as described above, when a structure is measured, the image of the structure can be displayed appropriately according to the definition. Thereby, when the size of structures is automatically measured by the ultrasound image diagnosis apparatus, the operator is no longer required to check whether each of the structures is displayed in an appropriate size on the display according to the measurement result. In particular, when there are a plurality of structures, the check work by the operator can be greatly reduced, which, as a result, contributes to the reduction of time taken to diagnose.

While certain embodiments have been described, these embodiments have been presented by way of example only, and are not intended to limit the scope of the inventions. Indeed, the novel embodiments described herein may be embodied in a variety of other forms; further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound image diagnosis apparatus, comprising processing circuitry configured to:
    detect a boundary of a plurality of structures in a subject based on volume data generated from a reflected signal of an ultrasound wave transmitted toward inside of the subject;
    measure an axial length of each of the plurality of structures based on the boundary detected;
    receive a selection of one of the plurality of structures, the selection being made according to a list of the respective measured axial lengths of the plurality of structures; and
    generate, for display, a cross section of the selected one of the plurality of structures from the volume data, the cross section being specified by a maximum axial length of the selected one of the plurality of structures.

2. The ultrasound image diagnosis apparatus of claim 1, wherein the plurality of structures are follicles.

3. The ultrasound image diagnosis apparatus of claim 1, wherein the processing circuitry is further configured to display the selected one of the plurality of structures using plural cross sections in the measured axial length, by moving or rotating a selected one of the plural cross sections.

4. The ultrasound image diagnosis apparatus of claim 3, wherein the processing circuitry is further configured to reflect result of the process in display of the selected one of the plurality of structures in other cross sections than the selected one to display the selected one of the plurality of structures in the cross sections.

5. The ultrasound image diagnosis apparatus of claim 3, wherein the processing circuitry is further configured to be capable of displaying a three-dimensional image with the cross sections on a display such that the three-dimensional image is oriented in the same direction as one of the cross sections selected by an operator.

6. The ultrasound image diagnosis apparatus of claim 5, wherein the processing circuitry is further configured to display the three-dimensional image as being oriented in the same direction as the one of the cross sections based on an input signal provided by the operator.

7. The ultrasound image diagnosis apparatus of claim 3, wherein the processing circuitry is further configured to display the cross sections of the selected one of the plurality of structures together with the axial length.

8. The ultrasound image diagnosis apparatus of claim 3, wherein the processing circuitry is further configured to display changes in the axial length of the selected one of the plurality of structures by moving one of the cross sections within a range illustrating the selected one of the plurality of structures.

9. The ultrasound image diagnosis apparatus of claim 3, wherein the selected one of the plural cross sections is an intersecting cross section.

10. A medical image diagnosis apparatus, comprising:
a display configured to display a medical image related to a structure based on volume data acquired by imaging a structure in a subject; and
processing circuitry configured to:
cause the display to display the medical image;
detect a boundary of a plurality of structures in a subject based on volume data generated from a reflected signal of an ultrasound wave transmitted toward inside of the subject;
measure an axial length of each of the plurality of structures based on the boundary detected;
receive a selection of one of the plurality of structures, the selection being made according to a list of the respective measured axial lengths of the plurality of structures; and
generate, for display, a cross section of the selected one of the plurality of structures from the volume data, the cross section being specified by a maximum axial length of the selected one of the plurality of structures.

11. The medical image diagnosis apparatus of claim 10, wherein the processing circuitry is further configured to display the selected one of the plurality of structures using plural cross sections in the measured axial length, by moving or rotating a selected one of the plural cross sections.

12. The medical image diagnosis apparatus of claim 11, wherein the processing circuitry is further configured to be capable of displaying a three-dimensional image with the cross sections on the display such that the three-dimensional image is oriented in the same direction as one of the cross sections selected by an operator.

13. The medical image diagnosis apparatus of claim 11, wherein the processing circuitry is further configured to display the cross sections of the selected one of the plurality of structures together with the axial length.

14. The medical image diagnosis apparatus of claim 11, wherein the processing circuitry is further configured to display changes in the axial length of the selected one of the plurality of structures by moving one of the cross sections within a range illustrating the selected one of the plurality of structures.

15. The medical image diagnosis apparatus of claim 11, wherein the selected one of the plural cross sections is an intersecting cross section.

16. A computer program product comprising a non-transitory computer-usable medium having computer-readable program codes that, when executed, cause a computer to:
detect a boundary of a plurality of structures in a subject based on volume data generated from a reflected signal of an ultrasound wave transmitted toward inside of the subject;
measure an axial length of each of the plurality of structures based on the boundary detected;
receive a selection of one of the plurality of structures, the selection being made according to a list of the respective measured axial lengths of the plurality of structures; and
generate, for display, a cross section of the selected one of the plurality of structures from the volume data, the cross section being specified by a maximum axial length of the selected one of the plurality of structures.

* * * * *